US011017899B2

(12) United States Patent
Carlsgaard et al.

(10) Patent No.: US 11,017,899 B2
(45) Date of Patent: *May 25, 2021

(54) PAIRING AND SYNCHRONIZING A MOBILE PHONE APPLICATION WITH A HANDHELD GLUCOSE METER

(71) Applicant: Roche Diabetes Care, Inc., Indianapolis, IN (US)

(72) Inventors: Eric S. Carlsgaard, Zionsville, IN (US); David B. Markisohn, Indianapolis, IN (US); Mark Mears, Westfield, IN (US)

(73) Assignee: Roche Diabetes Care, Inc., Indianapolis, IN (US)

(*) Notice: Subject to any disclaimer, the term of this patent is extended or adjusted under 35 U.S.C. 154(b) by 170 days.

This patent is subject to a terminal disclaimer.

(21) Appl. No.: 15/686,256

(22) Filed: Aug. 25, 2017

(65) Prior Publication Data

US 2017/0350899 A1 Dec. 7, 2017

Related U.S. Application Data

(63) Continuation of application No. 14/172,043, filed on Feb. 4, 2014.

(Continued)

(51) Int. Cl.
*G01N 33/66* (2006.01)
*G16H 40/63* (2018.01)
(Continued)

(52) U.S. Cl.
CPC ........... *G16H 40/63* (2018.01); *A61B 5/0002* (2013.01); *A61B 5/14532* (2013.01);
(Continued)

(58) Field of Classification Search
CPC .. G06Q 50/24; G01N 33/48792; G01N 33/66; A61B 5/74; A61B 5/14532;
(Continued)

(56) References Cited

U.S. PATENT DOCUMENTS 7,254,159 B1 8/2007 Lavelle et al.
2006/0242268 A1 10/2006 Omernick et al.
(Continued)

FOREIGN PATENT DOCUMENTS

CN 102761437 A 10/2012
EP 2001188 A1 12/2008

OTHER PUBLICATIONS

OneTouch VerioSync: Blood Glucose Monitoring System—Owner's Booklet (34 pgs.) (2014).
U.S. Appl. No. 14/172,043, filed Feb. 4, 2014, Carlsgaard et al.

*Primary Examiner* — Rebecca M Fritchman (57) ABSTRACT

A diabetes management system includes a handheld medical device, a mobile computing device, and a diabetes management application. The handheld medical device is configured to determine, in response to a port receiving a test strip, whether an auto-send feature is enabled on the handheld medical device, determine whether the handheld medical device is paired with a mobile computing device, and selectively instruct a wireless transceiver to establish a wireless connection and communicate a glucose measurement and identifying information to the mobile computing device. The mobile computing device is configured to execute the diabetes management application. The diabetes management application is configured to process a plurality of glucose measurements and identifying information associated with each of a plurality of glucose measurements.

6 Claims, 9 Drawing Sheets

Related U.S. Application Data (60) Provisional application No. 61/816,225, filed on Apr. 26, 2013.

(51) Int. Cl.

| | | |
|---|---|---|
| *A61B 5/00* | (2006.01) | |
| *A61B 5/145* | (2006.01) | |
| *G16H 40/67* | (2018.01) | |
| *G01N 33/00* | (2006.01) | |
| *H04L 9/32* | (2006.01) | |

(52) U.S. Cl.
CPC ............. G01N 33/66 (2013.01); G16H 40/67 (2018.01); *A61B 5/74* (2013.01); *A61B 5/7475* (2013.01); *H04L 9/3249* (2013.01); *H04L 2209/88* (2013.01); *Y10T 436/144444* (2015.01)

(58) Field of Classification Search
CPC . A61B 5/7475; A61B 5/0002; G06F 19/3418; G06F 19/3406; Y10T 436/144444; H04L 2209/88; H04L 9/3249; G16H 40/63

USPC ........................................... 436/95; 422/68.1
See application file for complete search history.

(56) References Cited

U.S. PATENT DOCUMENTS

| | | |
|---|---|---|
| 2008/0312585 A1 | 12/2008 | Brukalo et al. |
| 2009/0061769 A1 | 3/2009 | Zimbric et al. |
| 2010/0115279 A1 | 5/2010 | Frikart et al. |
| 2010/0305421 A1 | 12/2010 | Ow-Wing |
| 2010/0331645 A1 | 12/2010 | Simpson et al. |
| 2011/0093287 A1 | 4/2011 | Dicks et al. |
| 2011/0320130 A1 | 12/2011 | Valdes et al. |
| 2012/0245447 A1* | 9/2012 | Karan ................ A61B 5/14532 600/365 |
| 2012/0274443 A1 | 11/2012 | Kai et al. |
| 2013/0059541 A1 | 3/2013 | Sloan et al. |
| 2013/0191335 A1 | 7/2013 | Tse et al. |
| 2013/0231760 A1* | 9/2013 | Rosen ..................... G06F 17/40 700/91 |
| 2013/0316649 A1 | 11/2013 | Newham |
| 2014/0238874 A1* | 8/2014 | Elder .................... G01J 1/4204 205/782 |

* cited by examiner

Pairing your meter

This on-time pairing will allow you to wirelessly transfer blood glucose (bG) values from your meter to your mobile device.

*For an optimal experience ensure that Auto-Send and Sync Time are enabled.*

Auto-Send

Have your Accu-Chek meter automatically send bG values to your mobile device after every measurement.

Sync Time

Have your Accu-Chek meter automatically get the time and date from your mobile device..

PAIRING AND SYNCHRONIZING A MOBILE PHONE APPLICATION WITH A HANDHELD GLUCOSE METER

CROSS-REFERENCE TO RELATED APPLICATIONS

This application is a continuation of U.S. Ser. No. 14/172,043, filed on Feb. 4, 2014, which claims the benefit of U.S. Provisional Application No. 61/816,225, filed on Apr. 26, 2013. The entire disclosure of the above applications are incorporated herein by reference.

FIELD

The present disclosure relates to techniques for pairing and synchronizing a mobile phone application with a handheld glucose meter.

BACKGROUND

Persons with diabetes have difficulty regulating blood glucose levels in their bodies. As a consequence, many of these persons carry specialized electronic meters, called blood glucose meters, which allow them to periodically measure their glucose levels and take appropriate action, such as administering insulin. These persons may also carry with them a portable communication device, such as a mobile phone, a personal digital assistant, a tablet or similar device. People often rely on their portable communication device as the primary means for planning, scheduling and communicating with others. As a result, most portable communication devices are equipped with sophisticated software which provides user-friendly means for viewing and inputting data. Accordingly, a person with diabetes may wish to wirelessly transmit the results of a blood glucose measurement from their glucose meter to their portable communication device in order, for example, to display, analyze or report on the data.

Therefore, it is desirable to develop improved techniques for pairing and synchronizing a mobile phone application with a blood glucose meter or other handheld medical devices.

This section provides background information related to the present disclosure which is not necessarily prior art.

SUMMARY

Persons with diabetes often carry a handheld glucose meter as well as a portable computing device, such as a mobile phone. Given the close proximity of these two devices, the portable computing device can serve as a data collector for the glucose measures taken by the glucose meter. Improved techniques are set forth for pairing and synchronizing an application residing on the mobile phone with the patient's handheld glucose meter.

A diabetes management system includes a handheld medical device, a mobile computing device, and a diabetes management application. The handheld medical device includes a port, configured to receive a test strip having a reaction site for receiving a sample of fluid from a patient. The handheld medical device also includes a blood glucose (bG) meter, cooperatively operable with a test strip inserted in the port, configured to measure glucose in a sample of fluid residing in the test strip and associate identifying information with the glucose measurement; a wireless transceiver cooperatively operable with the bG meter to communicate the glucose measurement and the identifying information via a wireless data link.

The handheld medical device further includes a user interface that selectively instructs the handheld medical device to initiate a pairing procedure in response to input received from a user and that displays a unique identifier associated with the handheld medical device. The handheld medical device also includes a first processor configured to determine, in response to the port receiving a test strip, whether an auto-send feature is enabled on the handheld medical device. The first processor is also configured to determine whether the handheld medical device is paired with a mobile computing device.

The first processor is further configured to selectively instruct the wireless transceiver to establish a wireless connection and communicate the glucose measurement and the identifying information in response to the determination of whether the auto-send feature is enabled and the determination of whether the handheld medical device is paired with a mobile computing device The mobile computing device comprising a second processor configured to execute the diabetes management application stored on an associated memory. The application is configured to process a plurality of glucose measurements and identifying information associated with each of the plurality of glucose measurements.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Figure 1:
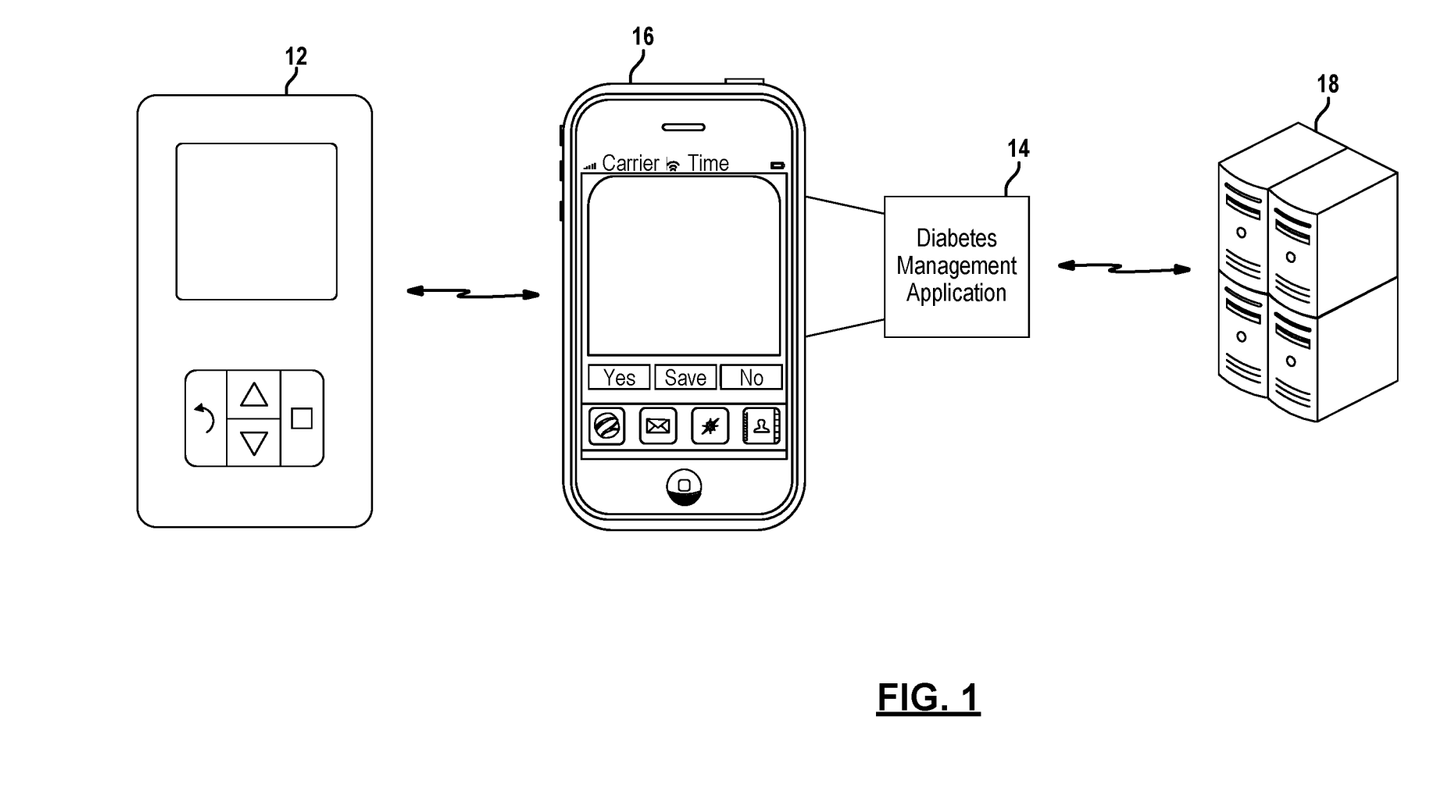
FIG. 1 is a diagram depicting a handheld glucose meter in data communication with a diabetes management application residing on a mobile phone.

FIG. 1 depicts an exemplary handheld glucose meter 12 in data communication via a wireless data link with a diabetes management application 14. The glucose meter 12 is configured to receive a sample of blood from a patient and determine a blood glucose measure for the patient from the blood sample. One or more blood glucose measures may in turn be transmitted over the wireless data link to the diabetes management application 14 for further processing. In an exemplary embodiment, the diabetes management application 14 resides on a mobile phone 16. In other embodiments, the diabetes management application may be native to a remote server with its user interface presented on the mobile phone 16. In some embodiments, data is transferred to and from the glucose meter 12 using the Bluetooth wireless technology standard (e.g., low energy feature of Bluetooth 4.0) although other types of communication transports are contemplated by this disclosure.

Figure 2:
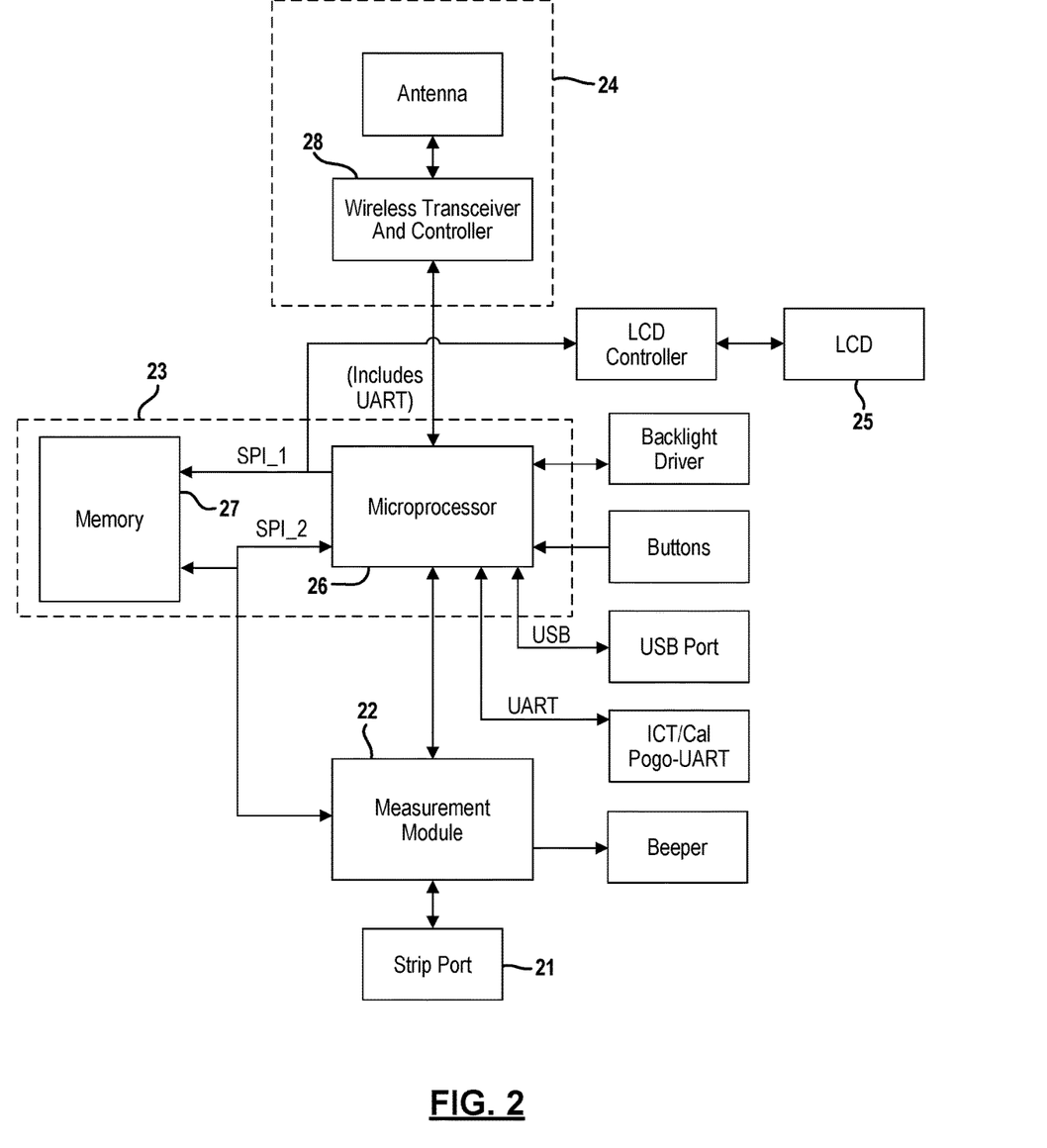
FIG. 2 is a block diagram of an exemplary hardware arrangement for the glucose meter.

FIG. 2 depicts an exemplary hardware arrangement for the glucose meter 12. The glucose meter 12 is comprised generally of a measurement module 22, a processing subsystem 23 and a communication subsystem 24. Each of these components is further described below. While the primary components are discussed herein, it is understood that other components (e.g., batteries) may be needed for the overall operational of the meter.

The measurement module 22 cooperatively interacts with a test strip inserted into a strip port 21 to determine a glucose measure from the sample of blood on the test strip. The measurement module 22 may include calibration information for the test strips being read by the meter. As used herein, the term module may refer to, be part of, or include an application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above. The term module may further include memory that stores code executed by the processor, where code, as used above, may include software, firmware, and/or microcode, and may refer to programs, routines, functions, classes, and/or objects.

The processing subsystem 23 is configured to receive the glucose measures from the measurement module 22 which may in turn be stored in memory by the processing subsystem 23. Glucose measures may also be displayed by the processing subsystem 23 on a display 25. The user can interact with the meter using various user interface components, such as buttons, switches, a speaker, a microphone, USB port, etc. Each of these components is interfaced with the processing subsystem 23. In an exemplary embodiment, the processing subsystem 23 includes a microprocessor 26 and one or more volatile and/or non-volatile memories 27 although other implementations are envisioned for the processing subsystem.

The processing subsystem 23 is also interfaced with the communication subsystem 24. In an exemplary embodiment, the communication module includes a wireless transceiver 28. The wireless transceiver operates to communicate the glucose measures and other data wirelessly via a data link to a remote device physically separated from the meter. The communication subsystem can also include an antenna, microcontroller, voltage and power control circuits and a flash memory device. Although a few primary components of the meter 12 are discussed herein, it is readily understood that other components (e.g., power source) may be needed to implement the meter.

Figure 3:
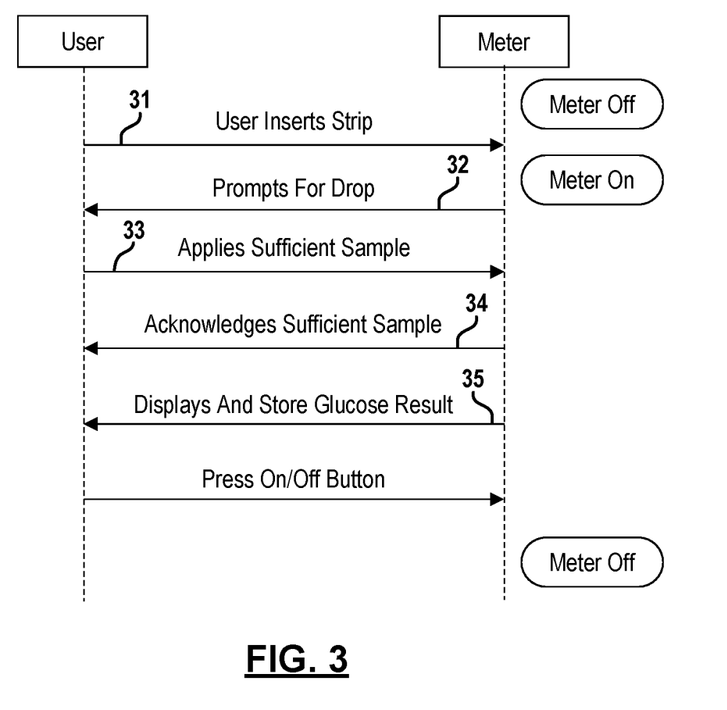
FIG. 3 is a sequence diagram illustrating an exemplary sequence for taking a blood glucose measure using the glucose meter.

FIG. 3 depicts an exemplary sequence for taking a blood glucose measure using the blood glucose meter 12. The user may insert a test strip at 31 into a port of the glucose meter. Insertion of the test strip prompts the glucose meter to power on. The user may alternatively power on the glucose meter using an on/off button. In this case, the glucose meter will prompt the user to insert a test strip. The user may also power on the glucose meter without having inserted a test strip into the meter. In any of these cases, the glucose meter may perform a quality check on the test strip inserted into the meter. Once the quality check has been completed, the meter is ready to perform a test.

To begin a test, the user is prompted at 32 for a sample of blood. In response to the prompt, the user provides a blood sample at 33 using the test strip, where the test strip includes a reaction site that receives the blood sample from the patient. Upon receipt of the blood sample, the glucose meter will proceed to analyze the blood sample in a manner readily known in the art. Before doing so, the glucose meter may acknowledge the sufficiency of the blood as indicated at 34.

During the analysis, a blood glucose measure is obtained from the blood sample. The blood glucose measure will be displayed to the user and stored on the glucose meter as indicated at 35. Stored glucose measures may be uploaded subsequently from the glucose meter in a batch manner to a physician's computer.

Figure 6A:
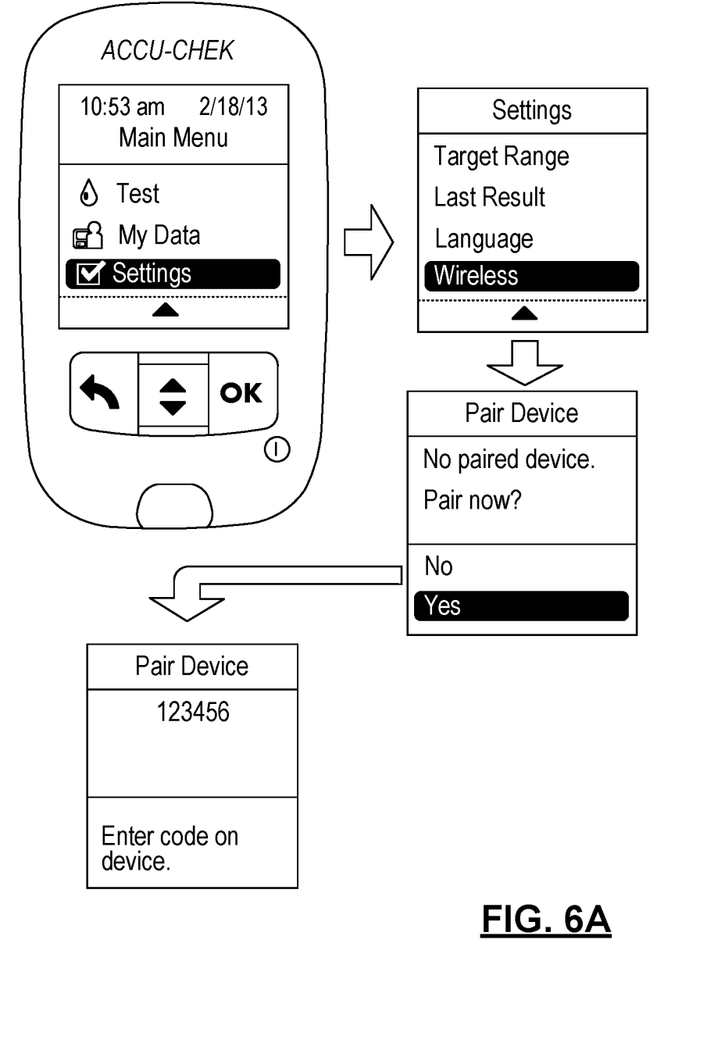
FIGS. 6A-6C depict example screens which may be presented during the pairing process.

Before the glucose meter 12 can interact with the diabetes management application 14, the glucose meter must be paired with the diabetes management application 14 or the device it resides on. In one embodiment, the user initiates the pairing process by interacting with the glucose meter. In particular, the user is prompted to pair with another device as shown in FIG. 6A. In response to an affirmative input, the glucose meter generates and displays a unique identifier for the meter. In some embodiments, the identifier may be a model and/or a serial number for the meter. The unique identifier can be used to identify the glucose meter to the mobile phone.

Figure 6B:
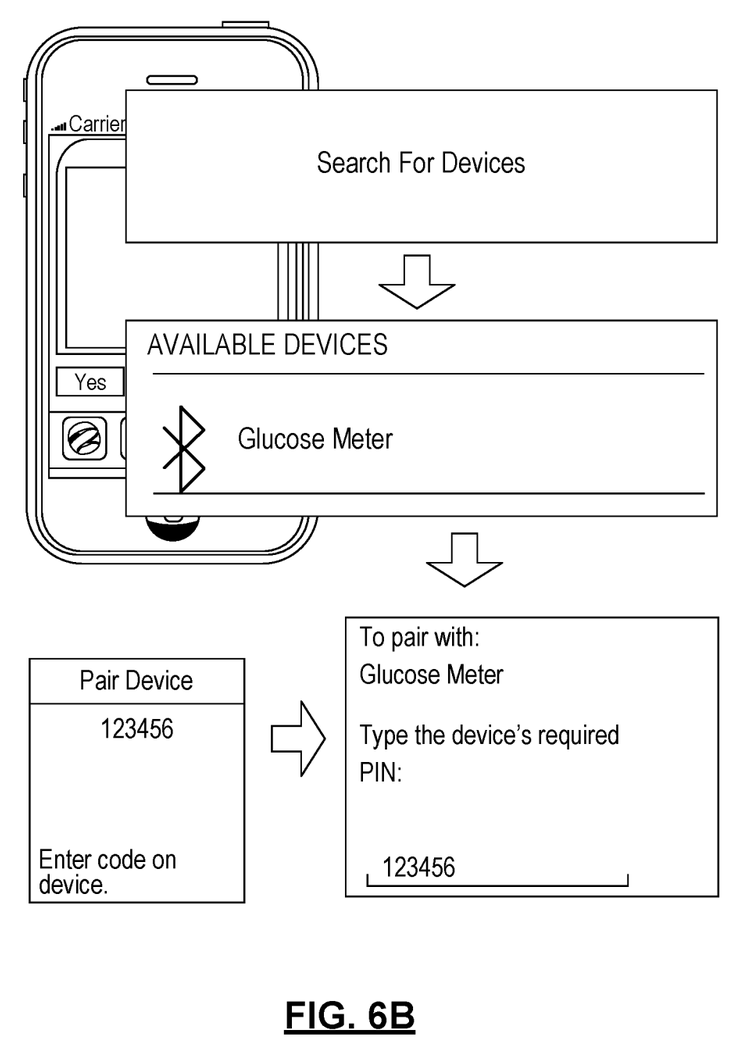

With reference to FIG. 6B, the user next interacts with the mobile phone to complete the pairing process. First, the user initiates a search of devices which are in wireless communication with the mobile phone. Available devices are displayed to the user and the user can then select the device the user desires to pair with. Upon selecting an available device, the user is requested to input the unique identifier as displayed on the glucose meter. Input of the identifier by the user initiates the pairing process between the devices. The pairing process may include verification of the inputted identifier as well as an exchange of authentication tokens (e.g., RSA key) by the two devices. Further details of an exemplary pairing process may be found in U.S. application Ser. No. 12/975,455 filed on Dec. 22, 2010 and which is incorporated in its entirety by reference herein.

Figure 6C:
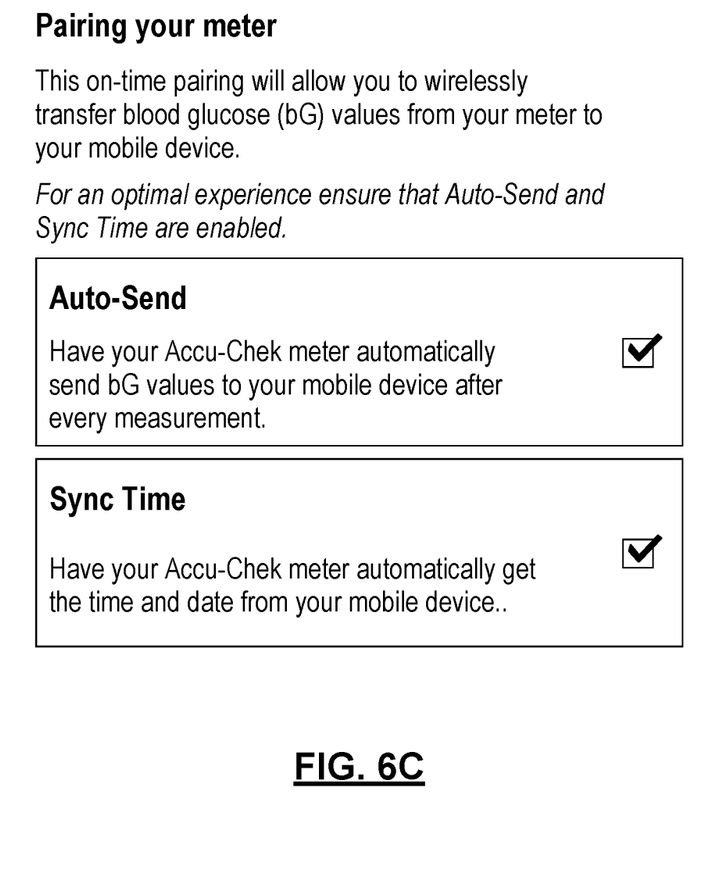

Once the two devices have been successfully paired, the user may be prompted, via the mobile phone, to enable select features associated with data transfer between the two devices as shown in FIG. 6C. For example, the user may be prompted on the mobile phone to enable an auto-send feature whereby blood glucose measures are automatically sent from the glucose meter 12 to the diabetes management application 14, for example immediately after the measures is taken. In another example, the user may be prompted to synchronize the time on the meter with the time from the mobile device. Techniques for implementing these features are further described below. It is envisioned that other types of features may be enabled as well.

Figure 4:
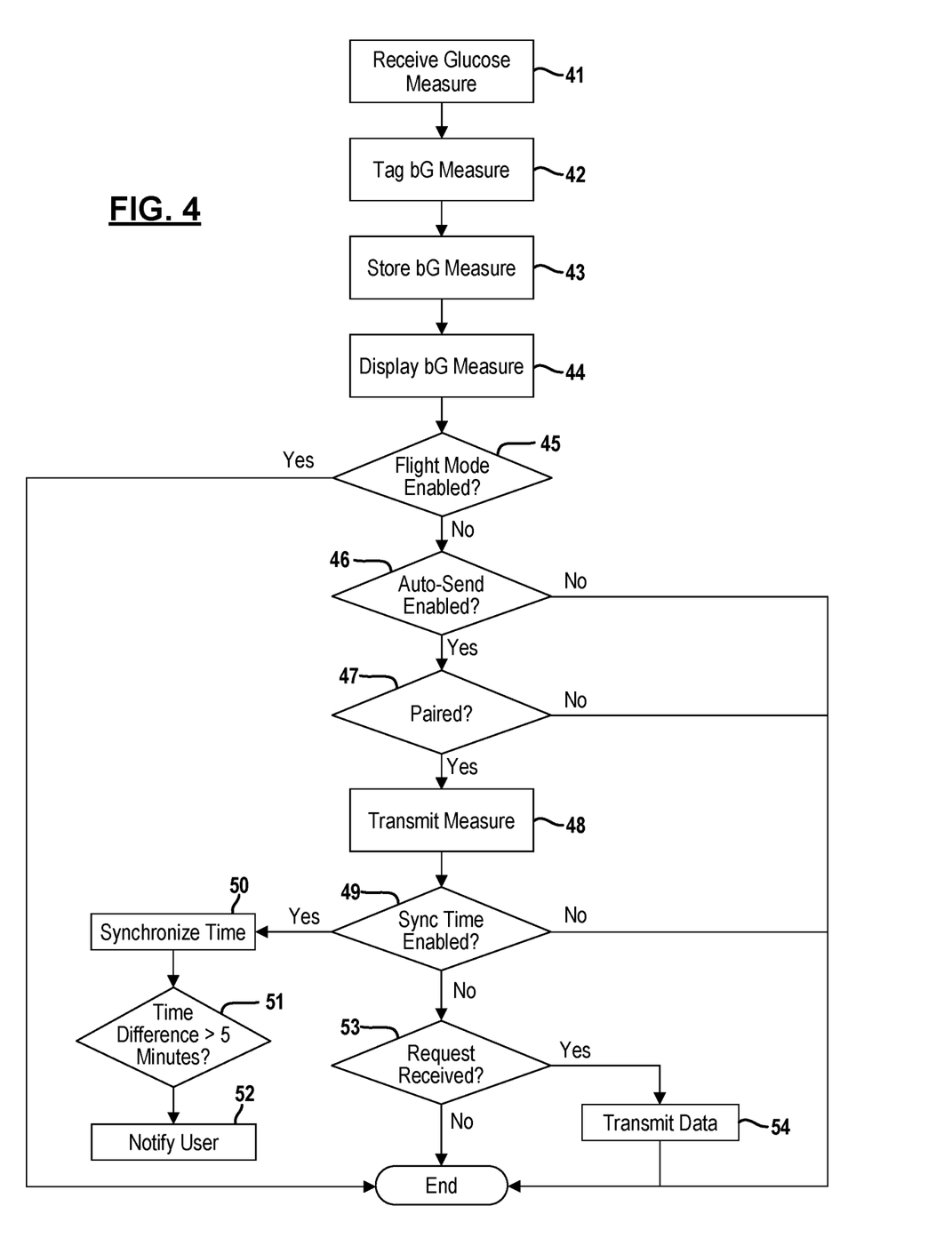
FIG. 4 is a flowchart illustrating an exemplary technique for transmitting blood glucose measures individually from the glucose meter.

Rather than sending blood glucose measures in a batch manner, the glucose meter may be configured to transmit blood glucose measures individually as shown in FIG. 4. The blood glucose measures may be transmitted, for example to a mobile phone or some other portable computing device carried by the user. Because the mobile phone is typically in close proximity to the user, it may be used as a data collector for the patient's blood glucose measures. A diabetes management application 14 residing on the mobile phone 16 can then be used for data analysis as well as other sophisticated diabetes management functions. Consequently, the processing power and memory available on the glucose meter can be streamlined, thereby reducing the cost of the glucose meter 12.

Upon determining a blood glucose measure, the blood glucose measure is first tagged at 42 with identifying information. The glucose measure may be tagged by the meter or tagged by the user. Identifying information may include but is not limited to a timestamp for when the measure was taken, a serial number for the meter, the meter type, other information pertaining to the test strip, and patient added comments. For example, the patient may add comments that include flags indicating the measurement was taken before a meal, after a meal, before bedtime, or other subjective health information. Of note, each blood glucose measure is also tagged with a unique sequence number assigned by the glucose meter. In one embodiment, a counter is incremented each time a glucose measure is taken and the value of the counter is assigned to the blood glucose measure. The sequence number may be used to retrieve missing data from the glucose meter as is further described below. Once tagged, the blood glucose measure is stored at 43 in a memory of the glucose meter and displayed to the user at 44 on a display of the glucose meter.

The glucose meter determines at 45 whether a flight mode is enabled. The flight mode may be enabled by the user when the user wishes to disable all network connectivity associated with the glucose meter. For example only, the user may enable the flight mode during take-off and landing of a plane in order to comply with flight regulations or requirements. When the glucose meter determines the flight mode is enabled, the glucose meter does not transmit blood glucose measurements.

When the glucose meter determines the flight mode is not enabled, the glucose meter determines at 46 whether an auto-send feature is enabled on the glucose meter. The auto-send feature is enabled by the user via the diabetes application management 14, described in further detail in relation to FIG. 6C. When the glucose meter determines the auto-send feature is not enabled, the glucose meter does not transmit blood glucose measurements.

Conversely, when the glucose meter determines the auto-send feature is enabled, the glucose meter determines at 47 whether it is paired via a wireless data link with another device, such as mobile phone 16. The current blood glucose measure is transmitted at 48 to the mobile phone when the glucose meter is paired to the mobile phone. While reference is made throughout this disclosure to a message being sent with a single glucose measure, it is envisioned that in some embodiments the message transmitted by the glucose meter can contain one or more glucose measures.

In one embodiment, the blood glucose measure is transmitted automatically and without user intervention. For example, after taking a glucose measure, the glucose measure is transmitted automatically after a predefined timeout period (e.g., five seconds) without receiving any input from the user. In another embodiment, the blood glucose measure is transmitted automatically in response to the user navigating away from the measurement result screen as will be further described below. In a similar manner, the blood glucose measure may be transmitted automatically in response to the meter being powered down by the user. It is envisioned that the mobile phone and/or the diabetes management application is authenticated with the glucose meter during the pairing process.

In some embodiment, the glucose meter may send the current time along with glucose measure to the mobile phone. The current time is maintained on the glucose meter by a clock residing therein. In some implementations, the current time includes a time from the clock residing on the meter plus an offset value. The offset value is the difference between a user adjustable display time on the meter and the clock residing within the meter. The diabetes management application may use the time from the meter when processing the glucose measure. For example, the diabetes management application may accept the glucose measure when the time falls within a certain allowable range, for example from the current time maintained by the mobile phone. Glucose measures having an associated time that falls outside an allowable range may be stored by the diabetes management application using the current time maintained by the mobile phone. Other uses for the time sent by the glucose meter are also envisioned by this disclosure.

In addition to transmitting the blood glucose measure, the glucose meter can synchronize its time with the mobile phone. During initial setup or thereafter, the glucose meter may be configured by the user, using either the glucose meter or the mobile phone, to synchronize its clock with the mobile phone. By enabling this time synchronization feature, the user is designating the mobile phone as the master device. Current time on the mobile phone is transmitted to the glucose meter during each data exchange. Because a user is interacting frequently with their meter, the time reported by the mobile phone is likely to be accurate. For example, the user may update a display time on the meter and change the offset value described above. The glucose meter will compare the current time on the mobile phone to the current time maintained by the glucose meter as indicated at 49. If the time synchronization feature has been enabled by the user and there is a difference between the two clocks, the glucose meter will set its clock to the current time of the mobile phone as indicated at 50.

Conversely, the glucose meter may retain its current time if time synchronization feature has not been enabled. If the time synchronization feature has been enabled by the user and the difference between the two clocks exceeds a the variance (e.g., 5 minutes) as indicated at 51, the glucose meter will set its clock to the current time of the mobile phone and notify the user as indicated at 52. In an alternative embodiment, the glucose meter will set its clock to the current time of the mobile phone if the difference between the two clocks is less than the variance threshold and the time synchronization feature is enabled. It is envisioned that other parameters, such as date/time format, target glucose ranges, hypo waning levels, etc., can also be synchronized between the two devices.

Time synchronization may occur during other types of data exchanges. For example, when the glucose meter is powered up, it may initiate a data session with the mobile phone. During this initial data session, the glucose meter may attempt to synchronize its time with the mobile phone in the manner set forth above. In this case, the time is synchronized independent from a blood glucose test.

During each data exchange, the glucose meter may also receive a request for missing glucose measures at 53 from the diabetes management application. In one embodiment, the request identifies any missing glucose measures by its sequence number as will be further described below. In response to receiving a request, the glucose meter will transmit the missing glucose measures at 54 to the diabetes management application. It is to be understood that only the relevant steps are discussed in relation to FIG. 4 but that other software-implemented instructions may be needed to transmit data from the glucose meter. In an exemplary embodiment, the method described above is implemented by a user interface module residing on the glucose meter.

Figure 5:
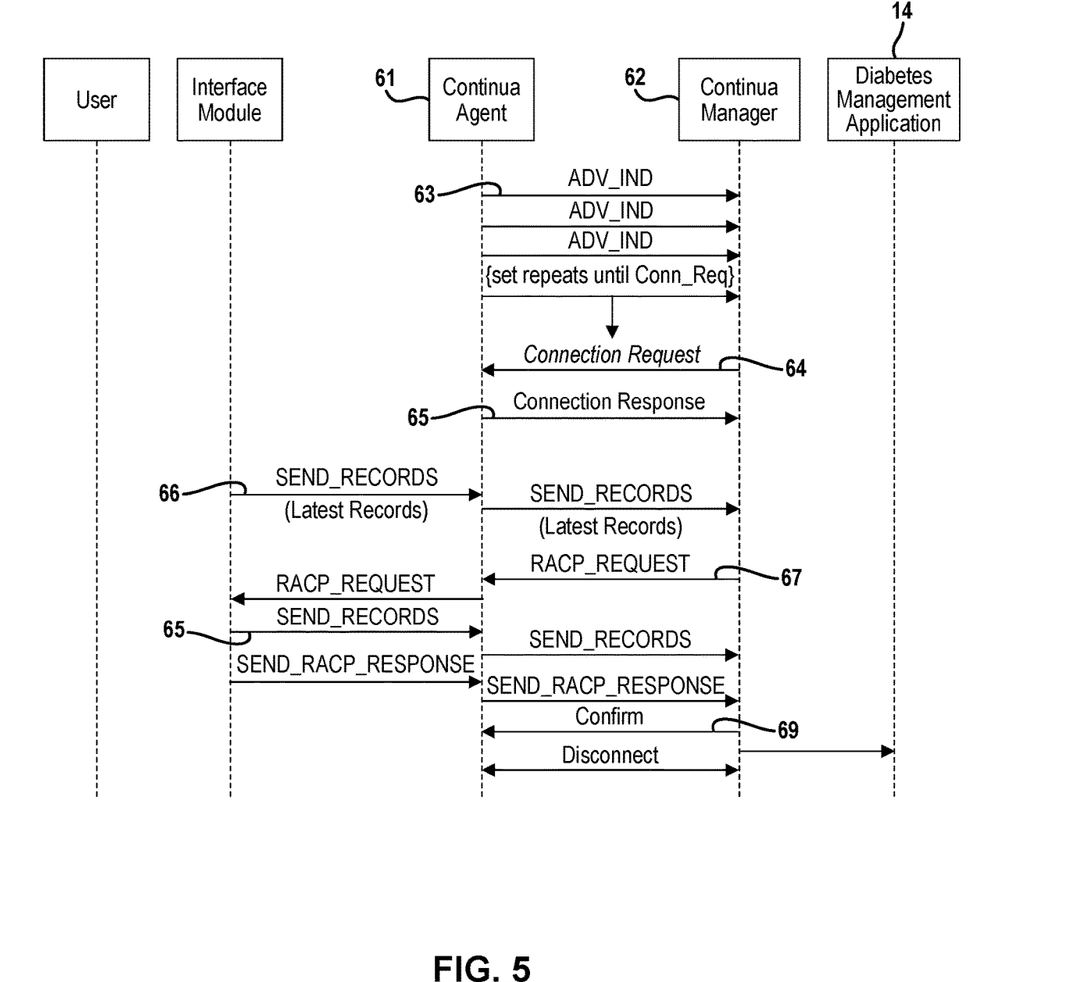
FIG. 5 is a sequence diagram depicting an exemplary data transmission between the glucose meter and the mobile phone.

FIG. 5 further illustrates an exemplary embodiment for implementing data transmission between the glucose meter 12 and the mobile phone 16. In this exemplary embodiment, data transmission occurs in accordance with IEEE standard 11073. The communication model employs the concept of "managers" and "agents". Agents are typically smaller personal health devices that lack processing power; whereas, managers tend to be more powerful computing devices such as a mobile phone or desktop computer. Each device performs certain roles in accordance with its designation. To implement its role, each device is configured with an interface component which implements the functions associated with its designated role. In this case, the glucose meter is configured with an agent component 61 and the mobile phone is configured with a manager component 62. While reference is made to a particular communication protocol, it is readily understood that concepts disclosed herein extend more broadly to other communication protocols.

To establish a communication session, the agent 61 initiates a connection with the manager 62 as indicated at 63. In response thereto, the manager 62 sends a connection request at 64 to the agent 61. In one embodiment, the connection request may include the current time maintained by the mobile phone. The current time may be used to synchronize the time on the glucose meter as described above. The agent 61 in turn responds to the connection request as indicated at 65, thereby establishing a connection between the agent and the manager.

Once a connection has been established, the current glucose measure can be sent automatically (or "pushed") from the glucose meter 12 to the mobile phone 16. Specifically, an interface module send the glucose measure to the agent 61 which in turn transmits the glucose measure to the manager 62 as indicated at 66, where the interface module is implemented by the processing subsystem 23. In some transport mechanisms (e.g., low energy feature of Bluetooth), the data manager or collector requests data (or "pulls") from the glucose meter. The current glucose measure can be sent automatically by the glucose meter to the diabetes management application 14 before any such request is received by the glucose meter as noted above. Alternatively, the current glucose meter can be sent by the glucose meter in response to receiving the request.

In addition, the manager 62 may send a request at 67 for any missing glucose measures to the glucose meter. The request is relayed by the agent 61 to the interface module which in turn handles the request. That is, the interface module retrieves any missing glucose measures identified in the request and sends those glucose measures back to the agent 61 as indicated at 65. The agent 61 then sends the missing glucose measures to the manager 62. The manager 62 may confirm receipt of the missing glucose measures at 69 and then proceed to terminate the connection with the agent. In other embodiments, it is envisioned that the agent may terminate the connection. In the event there are no missing glucose measures, the manager 62 can terminate the connection without sending additional requests to or otherwise polling the glucose meter and thereby conserve power and other resources.

In some instances, the data transmission from the meter to the mobile phone may be unsuccessful. The meter may be configured to periodically attempt to resend the glucose measure to the mobile phone. If the user attempts to power down the meter before a successful data transmission, the meter may continue to periodically attempt to resend the glucose measure to the mobile phone. The next time the meter is powered up, the user may be presented a message that the glucose measure was successfully transmitted to the mobile phone. In the event the glucose measure has not yet been transmitted successfully, the user may be presented with a message indicating the same.

Figure 7:
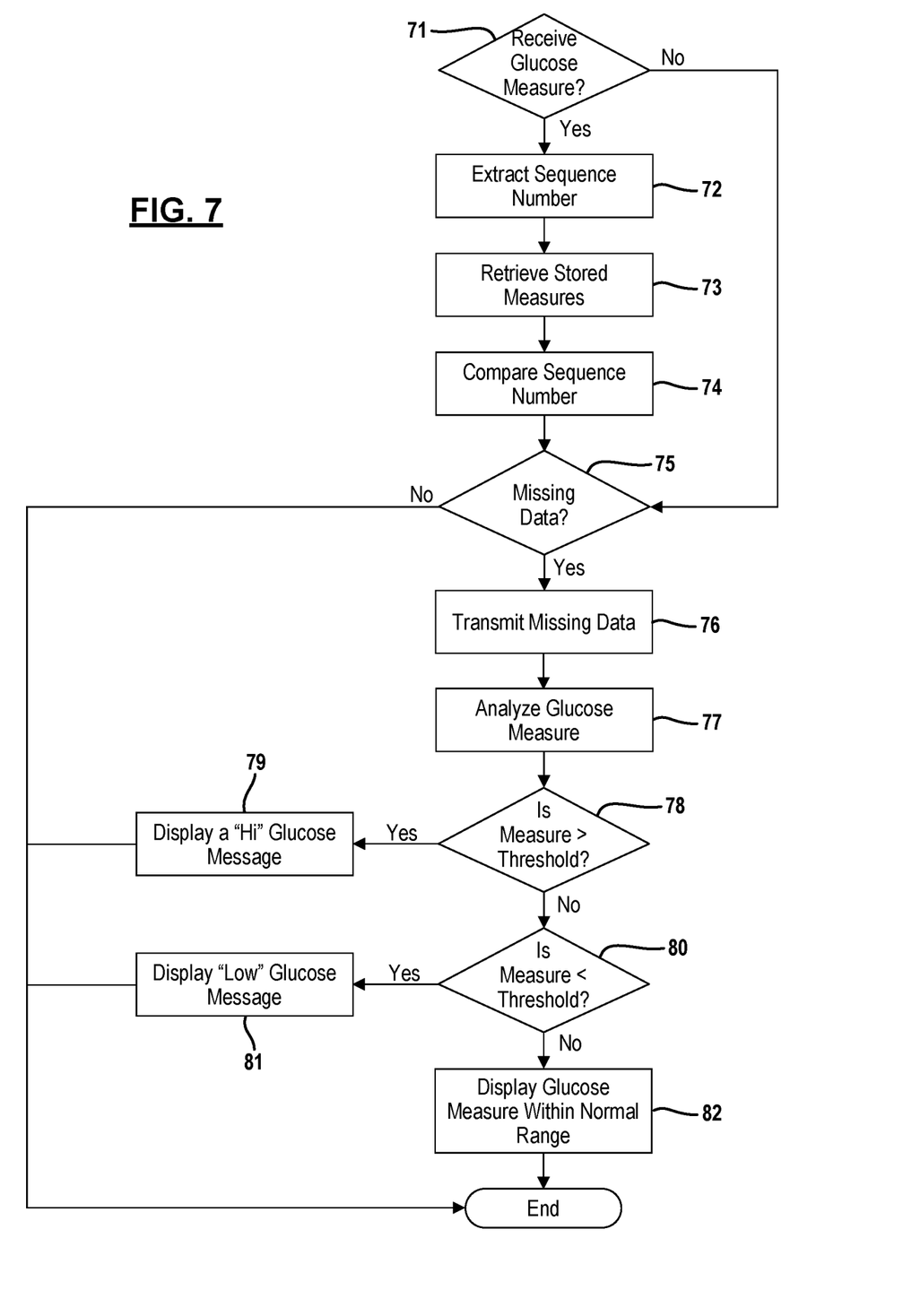
FIG. 7 is a flowchart illustrating an exemplary technique for processing glucose measures received by the diabetes management application.

FIG. 7 depicts an exemplary method for processing glucose measures received by the diabetes management application 14 residing on the mobile phone 16. In the exemplary embodiment, glucose measures are transmitted individually to the diabetes management application 14 as described in relation to FIG. 4. Additionally or alternatively, the glucose measures may be automatically transmitted to the diabetes management application 14 as described in relation to FIG. 6C. It is envisioned that other techniques for transmitting the glucose measure to the diabetes management application 14 are contemplated by this disclosure.

Upon receiving a glucose measure at 71, a sequence number associated with the glucose measure is first determined by the diabetes management application 14 residing on the mobile phone 16. A unique sequence number is assigned by the glucose meter to each glucose measure as described above. Thus, the sequence number associated with the glucose measure can be extracted at 72 from the data packet or message received from the glucose meter 12. In some embodiments, a series of glucose measures previously received from the glucose meter, along with their associated sequence numbers, may be stored in a memory device and thus accessible to the diabetes management application 14. In other embodiments, only the most recently received glucose measure and its sequence number is stored by the diabetes management application 14. In either case, the stored glucose measure(s) along with associated sequence number(s) are retrieved from memory.

A comparison is made at 74 between the sequence number extracted from the present glucose measure and the sequence numbers of the stored glucose measures. A request for missing glucose measures is transmitted by the diabetes management application 14 to the glucose meter 12 when an omission in the sequence is detected. For example, a request for missing glucose measures is transmitted when the extracted sequence number is 74 and the highest stored sequence number is either 71 or 72. Conversely, a request is not transmitted when the extracted sequence number is 74 and the highest stored sequence number is 73. Because this comparison is made for each glucose measure received by the diabetes management application 14, a comparison of the extracted sequence number only needs to be made to the highest stored sequence number.

In other embodiments, the diabetes management application 14 may analyze the series of glucose measure for omitted measures and send a request for each glucose measure missing from the series of glucose measures. The request for missing glucose measures can be transmitted in accordance with the protocol described in relation to FIG. 5.

In other embodiments, the diabetes management application 14 may display a message on the mobile phone 16 in response to the received glucose measure. The message may be a pop-up message that expires after a predetermined period or a message that requires the user to interact with the message. For example only, the message may require the user to acknowledge the message by touching the message.

In some embodiments, the diabetes management application 14 displays the message based on an analysis of the received glucose measure. The diabetes management application 14 analyzes the glucose measure at 77. The diabetes management application 14 compares the glucose measure to a first glucose threshold at 78. The first glucose threshold may be a predetermined glucose value or a glucose value derived from a plurality of variables. For example only, the glucose value may vary based on the time of day the glucose measure was taken, whether the glucose measure was taken before or after a meal, and a variety of patient statistics.

The diabetes management application 14 determines whether the glucose measure is greater than the first glucose threshold at 78. When the glucose measure is greater than the first glucose threshold, the diabetes management application 14 displays a message at 79 indicating to the user that the glucose measure is high. The message may also include instructions to the user to take appropriate action in order to reduce the user's glucose level.

In another embodiment, the diabetes management application 14 determines whether the glucose measure is high based on information tagged with the glucose measure. For example, the meter 12 may determine whether the glucose measure is greater than the first glucose threshold. When the glucose measure is greater than the first glucose threshold, the meter 12 flags the glucose measure as high. The diabetes management application 14 receives the glucose measure with the flag indicating the glucose measure is high. The diabetes management application 14 displays a message indicating to the user that the glucose measure is high.

When the glucose measure is not greater than the glucose threshold, the diabetes management application 14 determines at 80 whether the glucose measure is less than a second glucose threshold. The second glucose threshold may be a predetermined glucose value or a glucose value derived from a plurality of variables. It is understood that glucose measurements are analyzed over an acceptable range of glucose values. The range includes an upper limit and a lower limit. In the example embodiment, the first glucose threshold at 78 may be the same or different than the second glucose threshold at 80.

When the glucose measure is less than the second glucose threshold, the diabetes management application 14 displays a message at 81 indicating to the user that the glucose measure is low. The message may also include instructions to the user to take appropriate action in order to increase the user's glucose level.

In another embodiment, the diabetes management application 14 determines whether the glucose measure is low based on information tagged with the glucose measure. For example, the meter 12 may determine whether the glucose measure is less than the second glucose threshold. When the glucose measure is less than the second glucose threshold, the meter 12 flags the glucose measure as low. The diabetes management application 14 receives the glucose measure with the flag indicating the glucose measure is low. The diabetes management application 14 displays a message indicating to the user that the glucose measure is low.

When the glucose measure is not less than the second glucose threshold, the diabetes management application 14 displays at 82 a message indicating the glucose measure is within a normal range. It is to be understood that only the relevant steps are discussed in relation to FIG. 7 but that other software-implemented instructions may be performed by the diabetes management application 14.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

What is claimed is:

1. A diabetes management system, comprising:
a handheld medical device that includes:
- a port configured to receive a test strip, the test strip having a reaction site for receiving a sample of fluid from a patient;
- a measurement module cooperatively operable with a test strip inserted in the port and configured to measure glucose in a sample of fluid on the test strip;
- a wireless transceiver; and
- a communication module interfaced with the measurement module and cooperatively operable with the wireless transceiver, the communication module is configured to determine whether the handheld medical device is paired over a wireless communication link with a mobile computing device and, in response to a determination that the handheld medical device is paired with the mobile computing device, communicate the glucose measurement to the mobile computing device;
- wherein the communication module is configured to determine whether the sync time feature is enabled and to receive a current time from the mobile computing device,
- wherein the communication module, in response to a determination that the handheld medical device is paired with the mobile computing device and a determination that the sync time feature is enabled, is further configured to compares the current time from the mobile computing device to a current time on the handheld medical device and sets a clock on the handheld medical device to the current time from the mobile computing device when a difference between the current time from the mobile computing device and the current time on the handheld medical device exceeds a variance and without contemporaneous input from user of the handheld medical device.

2. The diabetes management system of claim 1 wherein the communication module is further configured to, in response to a determination that the sync time feature is disabled, retain current time on the handheld medical device.

3. The diabetes management system of claim 1 wherein the communication module is further configured to determine whether an auto send feature is enabled and, in response to a determination that the handheld medical device is paired with the mobile computing device and a determination that the auto send feature is enabled, communicate the glucose measurement to the mobile computing device.

4. The diabetes management system of claim 1 wherein the communication module is further configured to determine whether a test strip is received in the port and
- in response to a determination that a test strip is received in the port, determine whether an auto-send feature is enabled;
- in response to a determination that a test strip is received in the port, determine whether the handheld medical device is paired with a mobile computing device; and
- in response to a determination that both the auto-send feature is enabled and the handheld medical device is paired with the mobile computing device, communicate the glucose measurement to the mobile computing device.

5. The diabetes management system of claim 1 further comprises a diabetes management application residing on the mobile computing device, wherein the diabetes management application is configured to receive the glucose measurement and display the glucose measurement on a display of the mobile computing device.

6. The diabetes management system of claim 5 wherein the diabetes management application transmits the current time from the mobile computing device to the handheld medical device during a data exchange in which the glucose measurement is communicated to the mobile computing device.

* * * * *